(12) United States Patent
Lewis et al.

(10) Patent No.: US 6,528,674 B1
(45) Date of Patent: Mar. 4, 2003

(54) METHOD FOR PREPARING A CONTACT MASS

(75) Inventors: Larry Neil Lewis, Scotia, NY (US); William Jessup Ward, Niskayuna, NY (US); John Matthew Bablin, Amsterdam, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/553,912

(22) Filed: Apr. 20, 2000

(51) Int. Cl.⁷ .................................................. C02F 7/16
(52) U.S. Cl. .................................. 556/472; 252/182.32
(58) Field of Search ...................... 252/182.32; 556/472

(56) References Cited

U.S. PATENT DOCUMENTS

| | | |
|---|---|---|
| 2,380,995 A | 8/1945 | Rochow |
| 2,464,033 A | 3/1949 | Gilliam |
| 4,500,724 A | 2/1985 | Ward, III et al. |
| 5,250,716 A * | 10/1993 | Mi .............................. 556/472 |
| 5,847,181 A | 12/1998 | Nakauishi et al. |
| 5,973,177 A * | 10/1999 | Kulvila et al. ............... 556/472 |
| 6,005,130 A | 12/1999 | Lewis et al. |
| 6,057,469 A * | 5/2000 | Margaria et al. .... 252/182.32 X |

FOREIGN PATENT DOCUMENTS

| | | |
|---|---|---|
| EP | 0028009 | 6/1981 |

OTHER PUBLICATIONS

XP–002178208—Abstract—"Sintering Process of Copper and Silicon Mixed Powder Compacts", Yuji, Kenichi, Kenjiro, Fusao.

XP–002178209—Abstract—Direct Synthesis of Diphenyldichloro Rosilane–From Chlorobenzene Using as Silicon Source a Silicon–copper Alloy.

XP–002178142—"Kinetic Data and Mechanistic Model for the Reaction Between Si and CuCl", Weber, Vale, Souha, Gillot & Barrett, Soilid State Ionics 32/33 (1989) 250–257.

Rong et al., Aluminum as Promoter for the Direct Process to Methylcholorosilanes, Silicon for the Chemical Industry III, J. Kr. Tuset Eds. 199 (Trondheim, Norway, 1996).

Radosavlyevich et al., Influence of Some Admixtures on the Activity of Contact Masses for Direct Synthesis of Methylchlorosilanes, Institute of Inorganic Chemistry, Belgrade, Yugoslavia, (1965).

* cited by examiner

Primary Examiner—Paul F. Shaver
(74) Attorney, Agent, or Firm—Noreen C. Johnson; Christian G. Cabou

(57) ABSTRACT

A method for making an alkylhalosilane is provided wherein the method comprises heat treating silicon and a form of copper at a temperature greater than about 500° C. to produce a contact mass and effecting reaction between an alkyl halide and silicon in the presence of the contact mass to produce alkylhalosilane.

40 Claims, No Drawings

METHOD FOR PREPARING A CONTACT MASS

BACKGROUND OF THE INVENTION

The present invention relates to a method for preparing a contact mass. More particularly, the present invention relates to a method for preparing a contact mass for the direction reaction of powdered silicon, alkylhalide and copper catalyst.

Rochow, U.S. Pat. No. 2,380,995 discloses preparing a mixture of alkylhalosilanes by a direct reaction between powdered silicon and an alkylhalide in the presence of a copper-silicon alloy. This reaction is commonly referred to as the "direct method" or "direct process." The reaction can be summarized as follows:

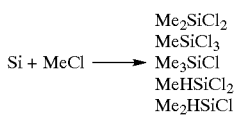

where Me is methyl.

In addition to the above methylchlorosilanes, "residue" is also formed during the production of methylchlorosilane crude. Residue means products in the methylchlorosilane crude having a boiling point greater than about 70° C., at atmospheric pressure. Residue consists of materials such as disilanes for example, symmetrical 1,1,2,2-tetrachlorodimethyldisilane; 1,1,2-trichlorotrimethydisilane; disiloxanes; disilmethylenes; and other higher boiling species for example, trisilanes; trisiloxanes; trisilmethylenes; etc.

As shown, the alkylhalosilanes formed by the direct reaction include dimethyldichlorosilane referred to as "D" or "Di" and methyltrichlorosilane, referred to as "T" or "Tri". These are the major products of the reaction, which typically produces dimethyldichlorosilane in a range between about 80% and about 88% and methyltrichlorosilane in a range between about 5% and about 10%. Dimethyldichlorosilane has the highest commercial interest. A T/D ratio is the weight ratio of methyltrichlorosilane to dimethyldichlorosilane in the crude methylchlorosilane reaction product. An increase in the T/D ratio indicates that there is a decrease in the production of the preferred dimethyldichlorosilane. Hence, the T/D product ratio is important and is the object of numerous improvements to the direct reaction.

Gilliam, U.S. Pat. No. 2,464,033 discloses using zinc in combination with copper catalyst as a promoter to achieve a higher selectivity of dimethyldichlorosilane. Gilliam discloses that a proportion in a range between about 2% and about 50% by weight of copper in elemental form or as the halide or oxide, and preferably 5 to 20% and zinc in a range between about 0.03% and about 0.75% by weight in the form of zinc halide, zinc oxide, or zinc metal, or mixture thereof, where the weights of copper and zinc are based on the weight of silicon, can be used as a promoter for making dialkyl substituted dihalogenosilanes, such as dimethyldichlorosilane in the direct reaction between silicon powder and methyl chloride.

Radosavlyevich et al., *Influence of Some Admixtures on the Activity of Contact Masses for Direct Synthesis of Methylchlorosilanes*, Institute of Inorganic Chemistry, Belgrade, Yugoslavia, (1965) discloses that micro quantities of silver added to contact masses resulting from the reaction of powdered silicon and methyl chloride in the presence of cuprous chloride decreases the yield of methylchlorosilanes, while tin and calcium chloride increase the rate of formation of methylchlorosilanes.

Rong et al., *Aluminum as Promoter for the Direct Process to Methylchlorosilanes, Silicon for the Chemical Industry III*, J. Kr. Tuset Eds. 199 (Trondheim, Norway, 1996) discloses adding solid aluminum compounds to improve reactivity and selectivity of the direct process. Ward et al., U.S. Pat. No. 4,500,724 discloses that tin and zinc are important in improving the direct method and can be controlled to provide improved alkylhalosilane product selectivity.

Methods are constantly being sought for making alkylhalosilanes that will enhance the rate of dimethyldichlorosilane formation, reduce the T/D weight ratio and maintain or reduce the percent by weight of products having a boiling point greater than about 70° C.

BRIEF SUMMARY OF THE INVENTION

The present invention improves direct process dimethyldichlorosilane formation, and selectivity while maintaining or substantially reducing residuals. According to the present invention, a selective contact mass is prepared by forming a mass of silicon with a form of copper and heat treating the mass at a temperature greater than about 500° C.

In an embodiment, the present invention relates to a method for making an alkylhalosilane, comprising heat treating silicon and a form of copper at a temperature greater than about 500° C. to produce a contact mass and effecting reaction of an alkyl halide in the presence of the contact mass to produce alkylhalosilane.

In another embodiment, the present invention relates to a reactor containing a contact mass prepared by forming a mass of silicon and a form of copper and heat treating the mass at a temperature greater than about 500° C.

In yet another embodiment, the present invention relates to an alkylhalosilane reactor containing a contact mass substantially free of forms of copper other than the eta ($Cu_3Si$) phase.

DETAILED DESCRIPTION OF THE INVENTION

In a typical instance, a mass for producing alkylhalosilanes is prepared by reacting silicon and cuprous chloride at a temperature in a range between about 280° C. and about 400° C. in a furnace until evolution of silicon tetrachloride ($SiCl_4$) ceases. The resulting solid contains silicon and copper and is called "contact mass." The contact mass is typically made prior to the step of contact with alkylhalide to generate alkylhalosilane. According to the present invention, silicon and a form of copper are heat treated to provide an improved contact mass.

According to the present invention, a form of copper is contacted with silicon to form a mass. The form of copper can provide a weight percent in a range between about 0.5% and about 10% relative to the entire contact mass. Preferably the amount of copper is in a range between about 1% and about 7% and more preferably in a range between about 2% and about 5%. The preparation of the contact mass proceeds according to the following equation (II):

at a temperature less than about 500° C. to form a contact mass.

The mass is then heat treated at an elevated temperature. The heat treatment step comprises heating the mass to a temperature in a range between about 550° C. and about 1550° C. Preferably the heating is to a temperature in a range between about 850° C. and about 1250° C. and more preferably to a temperature in a range between about 975° C. and about 1125° C. The heating is conducted for a period that varies with the temperature. Typically, the heating is conducted for a period in a range between about 0.01 hour and about 8 hours, preferably in a range between about 0.05 hours and about 4 hours and more preferably in a range between about 1 hour and about 3 hours. The heating is typically conducted with a steady application of heat over the desired period. Alternatively, the heating step can be conducted by applying heat to the mass in multiple periods, in step elevations or in pulses or the like. The heating step is typically conducted under inert conditions, for example, by providing a nitrogen atmosphere or the like.

Carboxylic acid salts of copper are typically used as the copper source to make the contact mass for the process. Copper formate, copper acetate and copper oxalate are examples of suitable carboxylic acid salts. The granular material should exhibit a BET surface area in a range between about 0.5 meters$^2$/gram and about 20 meters$^2$/gram by the nitrogen adsorption method.

Partially oxidized copper can also be the copper source to make the contact mass. Where the copper contains a level of tin relative to copper that exceeds a required range to make a satisfactory catalyst, a copper substantially free of tin can be alternated to purge excess tin, or mixtures of tin containing copper and copper substantially free of tin can be used to maintain a desired tin concentration in the resulting catalyst. "Substantially free of tin" as used herein refers to tin being present in an amount less than about 300 ppm. An example of a partially oxidized copper that can be used to make the contact mass comprises CuO in a range between about 32% and about 33%, $Cu_2O$ in a range between about 57% and about 59%, Cu in a range between about 5% and about 10% Cu, 350 parts per million (ppm) Fe, 54 ppm Sn, 22 ppm Pb, about 0.05% insolubles and less than about 20 ppm Bi or Ti. All percentages are by weight of the total mass of the partially oxidized copper.

Particulated cupric chloride, cuprous chloride, particulated copper metal can be utilized in making the contact mass. Zinc metal, halides of zinc, for example zinc chloride and zinc oxide have been found effective as components of the copper catalyst of the mass. Tin metal dust (−325 ASTM mesh), tin halides, such as tin tetrachloride, tin oxide, tetramethyl tin, and alkyl tin halide also can be used as a source of tin for making a catalyst component of the mass.

Silicon used in the contact mass can have an iron (Fe) content in a range between about 0.1% and 1% by weight based on total silicon, calcium (Ca) content in a range between about 0.01% and 0.2% by weight based on total silicon, and an aluminum (Al) content in a range between about 0.02% and 0.5% by weight based on total silicon. The silicon typically has a particle size below about 700 microns, with an average size greater than about 20 microns and less than about 300 microns. The mean diameter of the silicon particles is preferably in the range between about 100 microns and about 150 microns. Silicon is usually obtained at a purity of at least 98% by weight of silicon and it is then comminuted to particles of silicon in the above-described range for preparation of the contact mass.

Once the contact mass is formed, $Cu_3Si$, which is also referred to as eta-phase, is the predominant form of copper in the contact mass. The elevated temperature heat treatment of the contact mass substantially increases the eta-phase of copper found in the total contact mass.

The term "selectivity" herein means the ability of a catalyst to maximize the production of dimethyldichlorosilane, as shown for example by a reduction in the value of the T/D ratio and a reduction in the % residue.

Herein, the term "effective amount," means that amount of a substance capable of either increasing the yield of the alkylhalosilane product or increasing selectivity toward dimethyldichlorosilane.

The T/D weight ratio of the methylchlorosilane reaction product is of interest. The T/D ratio is the ratio of the methyltrichlorosilane to dimethyldichlorosilane in the crude methylchlorosilane reaction product. Accordingly, an increase in the T/D ratio indicates that there is a decrease in the production of the preferred dimethyldichlorosilane.

Although methyl chloride is preferably used in the practice of the present invention, other $C_{(1-4)}$ alkylchlorides, for example ethyl chloride, propyl chloride, etc., can be used. Correspondingly, the term "alkylhalosilane" includes dimethyldichlorosilane, which is the preferred methylchlorosilane, and a variety of other silanes such as tetramethylsilane, trimethylchlorosilane, methyltrichlorosilane, silicon tetrachloride, trichlorosilane, methyldichlorosilane and dimethylchlorosilane.

The alkylhalosilane reaction is typically run with a promoter such as aluminum or phosphorus. The aluminum can be added in an amount to provide to the entire contact mass between about 100 parts per million (ppm) and about 1000 parts per million, and alternatively in a range between about 300 parts per million and about 700 parts per million. When phosphorus is a component of the contact mass, it is typically present in a range between about 100 parts per million and about 1000 parts per million relative to the entire contact mass. Zinc can be added in an amount in a range between about 0.01% and 1% by weight relative to the contact mass in addition to tin in an amount between about 10 parts per million and 100 parts per million.

The aluminum can be supplied from various sources. "Source" as used herein refers to the chemical compound that provides the necessary element or elements for the mass. The source of aluminum can be aluminum powder, various alloys including but not limited to copper-aluminum alloy, silver-aluminum alloy, silicon-aluminum alloy, magnesium-aluminum alloy or combinations thereof.

When phosphorus is added to the contact mass, it can be supplied from a variety of sources. For instance, the phosphorus source can be copper phosphide, zinc phosphide, phosphorus trichloride, alkylphosphines such as triethylphosphine or trimethylphosphine or combinations thereof. With or without added phosphorus, the T/D ratio decreases with the addition of the heat treated contact mass.

The present invention commonly may be practiced in a fixed bed reactor. However, the process can be conducted in other types of reactors, such as fluid bed and stirred bed. More specifically, the fixed bed reactor is a column that contains silicon particles through which alkylhalide gas passes. A stirred bed is similar to a fixed bed in which there is mechanical agitation of some sort in order to keep the bed in constant motion. A fluidized bed reactor includes a bed of silicon particles, catalyst particles and co-catalyst particles, which is fluidized; i.e., the silicon particles are suspended in the gas, typically methylchloride as it passes through the reactor. Reaction typically occurs under semi-continuous conditions or in batch mode at a temperature between about 250° C. and about 350° C., and preferably between about 280° C. and about 320° C. It is also advisable to carry out the reaction under a pressure in a range between about 1 atmospheres and about 10 atmospheres in instances where a fluid bed reactor is used since higher pressure increases the rate of conversion of methylchloride to methylchlorosilanes. Desirably, the pressure is in a range between about 1.1 atmospheres and about 3.5 atmospheres and preferably in a range between about 1.3 atmospheres and about 2.5 atmospheres.

The expression "semi-continuous conditions" with respect to the description of the reaction of methyl chloride and a contact mass means that reaction solids are added and the reactor is run until about 50% of the silicon has been utilized. After about 50% utilization, additional reactants of silicon, copper catalyst, co-catalyst and promoters may be added. With a batch mode reaction, all of the solid components are combined and reacted with any reactants until most of the reactants are consumed. In order to proceed the reaction has to be stopped and additional reactants added. A fixed bed and stirred bed are both run under batch conditions.

A contact mass of powdered silicon, with copper catalyst can be made prior to contact with methyl chloride to facilitate the generation of alkylhalosilanes. Preferably, a reactive copper compound, such as cuprous chloride, etc., can be mixed with appropriate amounts of powdered silicon, tin or zinc and heated to a temperature of about 280° to 400° C. and then heat treated according to the invention.

The contact mass of the present invention can be made by introducing the above-described components into the reactor separately or as a mixture, master batch, alloy or blend of two or more of the various components in elemental form or as compounds or mixtures and in situ heat treated. Alternatively, a bed can be formed and heat treated prior to charge to a reactor vessel.

Features of the invention are illustrated in the following examples, which by way of example without limitation describe preferred embodiments of the present invention.

EXAMPLE 1

A methylchlorosilane reaction was carried out in a fixed bed reactor. The fixed bed comprised a silicon contact mass containing 5% copper catalyst, 0.05% by weight zinc dust, and 50 ppm tin dust. The bed was reacted with methyl chloride at 310° C. The reaction was first run as a control with a bed of silicon and 5% copper as copper chloride. In a second run, the contact mass was prepared by reaction between copper chloride and silicon in a furnace under a flow of inert gas for approximately 1–2 hours at 1100° C.

It was unexpectedly found that the methylchlorosilane reaction using preheated copper/silicon contact mass gave significantly higher selectivity for dimethyldichlorosilane than the control run using copper chloride. Additionally, use of pre-heated copper/silicon contact mass gave methylchlorosilane product mixtures that were low in by-product MeHSiCl$_2$ and MeH$_2$SiCl and residue.

Two other runs were conducted with phosphorus as a promoter first with a silicon and copper chloride catalyst and then with a pre-heated copper/silicon contact mass. Almost no Si-H-containing species (MeHSiCl$_2$ and MeH$_2$SiCl) were formed using the phosphorus promoter and preheated mass.

EXAMPLE 2

A methylchlorosilane reaction was carried out in a fluid bed reactor. In this Example, methylchloride was continuously introduced into a fluidized bed reactor having 20 grams of mass of copper and silicon powder comprising 5% copper catalyst, 0.05% zinc dust and 50 to 75 ppm tin dust. The contact mass bed was reacted with methyl chloride at 310° C. and crude reaction product was collected and analyzed with gas chromatography over a 24 to 28 hour period.

The reaction was first run as a control with a bed of silicon and 5% copper as copper chloride that was pre-treated into a contact mass at 350° C. The reaction was also run as a control with a bed of silicon and 5% copper as a mixed copper oxide that was prepared in the fluid bed reactor at 310° C. The reaction was also run as a control with a bed of silicon and 5% copper as copper chloride that was prepared in the fluid bed reactor at 310° C.

In another run, a mass was prepared by reaction between copper chloride and silicon at 350° C. The mass was then treated in a furnace under a flow of inert gas for 1.5 hours at 1100° C. The resulting heat treated mass was then used in the same fluid bed methylchlorosilane reaction.

Values obtained from the foregoing runs are reported in the following Table 1 and illustrate the improvement obtained by heat treatment according to the invention. The values were determined at approximately 1 to 2% Silicon Utilization (a measure of reaction completion wherein an approximate amount of silicon has reacted).

TABLE 1

| Copper | Temperature | D | T | MeHSiCl$_2$ | MeH$_2$SiCl | Residue |
| --- | --- | --- | --- | --- | --- | --- |
| CuCl | 350° C. | 77.7 | 10 | 5 | 0.7 | 6.0 |
| Cu$_x$O | In Situ 310° C. | 77.7 | 6.1 | 3.9 | 0.6 | 11.3 |
| CuCl | In Situ 310° C. | 84.6 | 7.3 | 4 | 0.9 | 2.6 |
| CuCl | 350/1100° C. | 86.7 | 4.4 | 3.5 | 0.1 | 5.3 |

Crude values at approximately 18 to 22% Silicon Utilization also demonstrated the value of heat treatment, as shown in Table 2.

TABLE 2

| Copper | Temperature | D | T | MeHSiCl$_2$ | MeH$_2$SiCl | Residue |
| --- | --- | --- | --- | --- | --- | --- |
| CuCl | 350° C. | 85.1 | 5.1 | 3.1 | 1 | 5.3 |
| Cu$_x$O | In Situ 310° C. | 85.0 | 5.7 | 3.7 | 0.6 | 4.9 |
| CuCl | In Situ 310° C. | 89.1 | 3.5 | 2.3 | 0.6 | 4.2 |
| CuCl | 350/1100° C. | 90.1 | 2.6 | 2.2 | 0.2 | 4.3 |

Average crude values for approximately 20% Silicon Utilization also demonstrated the value of heat treatment, as shown in Table 3.

TABLE 3

| Copper | Temperature | D | T | MeHSiCl$_2$ | MeH$_2$SiCl | Residue |
| --- | --- | --- | --- | --- | --- | --- |
| CuCl (4 runs) | 350° C. | 85.0 | 4.9 | 3.2 | 1 | 6.1 |
| Cu$_x$O (3 runs) | In Situ 310° C. | 84.5 | 6.1 | 3.7 | 0.7 | 4.7 |
| CuCl (3 runs) | In Situ 310° C. | 88.2 | 3.9 | 2.3 | 1.0 | 4.3 |
| CuCl | 310/1100° C. | 90.1 | 2.6 | 2.2 | 0.2 | 4.3 |

The above Examples show that a significant dimethyldichlorosilane increase is obtained with a heat treated contact mass according to the present invention.

EXAMPLE 3

A methylchlorosilane reaction was carried out in a fixed bed reactor. The bed, 6 grams, comprised a silicon contact mass containing 5% copper, 0.5% zinc dust and 50 to 75 ppm tin dust. The bed was reacted with methyl chloride at 310° C. The reaction was first run as a control with a bed of silicon and 5% copper as copper chloride that was pretreated into a contact mass at 350° C. The reaction was also run as a control with a bed of silicon and 5% copper as copper chloride that was decomposed in the fluid bed reactor at 315° C. In another run, the bed mass was first prepared by reaction at 350° C. between copper chloride and silicon to form a contact mass, which was then treated in a furnace under a flow of inert gas for 1.5 h at 1100° C.

Crude values at approximately 20% Silicon Utilization shown in Table 4 also demonstrate the value of heat treatment.

TABLE 4

| Copper | Temperature | D | T | $MeHSiCl_2$ | $MeH_2SiCl$ | Residue |
|---|---|---|---|---|---|---|
| CuCl (4 runs) | 350° C. | 88.0 | 5.7 | 2.4 | 1.0 | 2.8 |
| CuCl (2 runs) | In Situ 315° C. | 87.5 | 5.3 | 2.7 | 0.5 | 3.7 |
| CuCl | 310/1100° C. | 92.5 | 4.0 | 2.2 | 0.2 | 1.0 |

While preferred embodiments of the invention have been described, the present invention is capable of variation and modification and therefore should not be limited to the precise details of the Examples. The invention includes changes and alterations that fall within the purview of the following claims.

What is claimed is:

1. A method of preparing a contact mass, comprising the steps of:
   (I) forming a mass by mixing silicon and a form of copper and heating to a temperature less than about 500° C.; and
   (II) heat treating said mass formed in step (I) at a temperature greater than about 500° C. wherein said heat treatment increases a $Cu_3Si$ form of copper in said contact mass.

2. An alkylhalosilane reactor containing a contact mass substantially free of forms of copper other than the eta ($Cu_3Si$) phase.

3. The method of claim 1, wherein said heat treating comprises heating said contact mass at a temperature in a range between about 550° C. and about 1550° C.

4. The method of claim 1, wherein said heat treating comprises heating said contact mass at a temperature in a range between about 850° C. and about 1250° C.

5. The method of claim 1, wherein said heat treating comprises heating said contact mass at a temperature in a range between about 975° C. and about 1125° C.

6. The method of claim 1, wherein said heat treating comprises heating said contact mass at a temperature in a range between about 550° C. and about 1550° C. for a period of time in a range between about 0.01 hours and about 8 hours.

7. The method of claim 1, wherein said heat treating comprises heating said contact mass at a temperature in a range between about 550° C. and about 1550° C. for a period of time in a range between about 0.5 hours and about 4 hours.

8. The method of claim 1, wherein said heat treating comprises heating said contact mass at a temperature in a range between about 550° C. and about 1550° C. for a period of time in a range between about 1 hour and about 3 hours.

9. The method of claim 1, wherein said heat treating results in a contact mass substantially free of forms of copper other than the eta ($Cu_3Si$) phase.

10. The method of claim 1, wherein said contact mass comprises copper in a range between about 0.5% and about 10% by weight relative to the entire contact mass.

11. The method of claim 1, wherein said contact mass comprises copper in a range between about 1% and about 7% by weight relative to the entire contact mass.

12. The method of claim 1, wherein said contact mass comprises copper in a range between about 2% and about 5% by weight relative to the entire contact mass.

13. The method of claim 1, wherein said heat treating comprises a steady application of heat over a period.

14. The method of claim 1, wherein said heat treating comprises applying heat in multiple periods, in step elevations, or in pulses.

15. The method of claim 1, wherein said heat treating is conducted in an inert gas atmosphere.

16. The method of claim 15, wherein said inert gas atmosphere is a nitrogen atmosphere.

17. The method of claim 1, wherein said mass comprises powdered silicon and a copper-zinc-tin catalyst.

18. A method for making an alkylhalosilane, comprising forming a mass by mixing silicon and a form of copper and heating to a temperature less than about 500° C. and heat treating said formed mass at a temperature of greater than about 500° C. to produce a contact mass wherein said heat treating increases an eta ($Cu_3Si$) phase of copper in said contact mass and effecting reaction between an alkyl halide and silicon in the presence of said contact mass to produce alkylhalosilane.

19. The method of claim 18, wherein said heat treating comprises heating said contact mass at a temperature in a range between about 550° C. and about 1550° C.

20. The method of claim 18, wherein said heat treating comprises heating said contact mass at a temperature in a range between about 850° C. and about 1250° C.

21. The method of claim 18, wherein said heat treating comprises heating said contact mass at a temperature in a range between about 975° C. and about 1125° C.

22. The method of claim 18, wherein said heat treating comprises heating said contact mass at a temperature in a range between about 550° C. and about 1550° C. for a period of time in a range between about 0.01 hours and about 8 hours.

23. The method of claim 18, wherein said heat treating comprises heating said contact mass at a temperature in a range between about 550° C. and about 1550° C. for a period of time in a range between about 0.5 hours and about 4 hours.

24. The method of claim 18, wherein said heat treating comprises heating said contact mass at a temperature in a range between about 550° C. and about 1550° C. for a period of time in a range between about 1 hour and about 3 hours.

25. The method of claim 18, wherein said heat treating results in a contact mass substantially free of forms of copper other than the eta ($Cu_3Si$) phase.

26. The method of claim 18, wherein contact mass comprises copper in a range between about 0.5% and about 10% by weight relative to the entire contact mass.

27. The method of claim 18, wherein contact mass comprises copper in a range between about 1% and about 7% by weight relative to the entire contact mass.

28. The method of claim 18, wherein contact mass comprises copper in a range between about 2% and about 5% by weight relative to the entire contact mass.

29. The method of claim 18, wherein said heat treating comprises a steady application of heat over a desired period.

30. The method of claim 18, wherein said heat treating comprises applying heat in multiple periods, in step elevations, or in pulses.

31. The method of claim 18, wherein said heat treating is conducted in an inert gas atmosphere.

32. The method of claim 31, wherein said inert gas atmosphere is a nitrogen atmosphere.

33. The method of claim 18, wherein said mass comprises powdered silicon and a copper-zinc-tin catalyst.

34. The method of claim 18, wherein said alkylhalide comprises methylchloride.

35. The method of claim 18, wherein said reaction is conducted in a fluid-bed reactor.

36. The method of claim 18, wherein said reaction is conducted in a fixed-bed reactor.

37. The method of claim 18, wherein said reaction is conducted in a stirred-bed reactor.

38. A fluid-bed reactor containing a contact mass prepared according to the method of claim 1.

39. A fixed-bed reactor containing a contact mass prepared according to the method of claim 1.

40. A stirred-bed reactor containing a contact mass prepared according to the method of claim 1.

* * * * *